United States Patent
Tsukada

[11] Patent Number: 5,817,067
[45] Date of Patent: Oct. 6, 1998

[54] CAP FOR MEDICAL APPLIANCE TO BE RETAINED IN HUMAN BODY

[75] Inventor: Osamu Tsukada, Nagano-ken, Japan

[73] Assignee: Tsukada Medical Research Co., Ltd., Tokyo, Japan

[21] Appl. No.: 603,076

[22] Filed: Feb. 20, 1996

[30] Foreign Application Priority Data

Dec. 1, 1995 [JP] Japan .................................... 7-314054

[51] Int. Cl.⁶ .................................................... A61M 5/00
[52] U.S. Cl. ............................................ 604/256; 604/278
[58] Field of Search .................................. 604/256, 278, 604/329; 600/29–33; 215/235, 237, 330; 220/230, 212.5, 335, 339, 375

[56] References Cited

U.S. PATENT DOCUMENTS

| | | |
|---|---|---|
| 2,932,545 | 4/1960 | Foley . |
| 3,058,472 | 10/1962 | Thornton, Jr. .......................... 604/256 |
| 3,419,008 | 12/1968 | Plishner .................................. 600/31 |
| 3,468,576 | 9/1969 | Beyer et al. . |
| 3,933,271 | 1/1976 | McGhie ................................. 220/335 |
| 3,952,726 | 4/1976 | Hennig et al. ......................... 128/1 R |
| 4,060,100 | 11/1977 | Miller et al. . |
| 4,110,552 | 8/1978 | Lombardi . |
| 4,154,226 | 5/1979 | Hennig et al. ......................... 128/1 R |
| 4,193,519 | 3/1980 | Dubach et al. ........................ 222/111 |
| 4,338,937 | 7/1982 | Lerman . |
| 4,346,810 | 8/1982 | Kneissl .................................. 215/237 |
| 4,386,714 | 6/1983 | Roberto et al. ....................... 220/339 |
| 4,417,890 | 11/1983 | Dennehey et al. . |
| 4,443,219 | 4/1984 | Meisch et al. . |
| 4,706,834 | 11/1987 | Farney et al. . |
| 4,944,732 | 7/1990 | Russo ................................... 604/247 |
| 4,963,132 | 10/1990 | Gibson . |
| 5,057,093 | 10/1991 | Clegg et al. ......................... 604/283 |
| 5,098,405 | 3/1992 | Peterson et al. . |
| 5,263,944 | 11/1993 | Vidal et al. . |
| 5,460,615 | 10/1995 | Storz ................................... 604/167 |
| 5,624,410 | 4/1997 | Tsukada et al. ...................... 604/256 |

FOREIGN PATENT DOCUMENTS 25 51 010 5/1977 Germany .
658 438 11/1986 Switzerland .

Primary Examiner—Wynn Wood Coggins
Assistant Examiner—Deborah Blyveis
Attorney, Agent, or Firm—Sughrue, Mion, Zinn, Macpeak & Seas, PLLC

[57] ABSTRACT

A cap (10) for a medical appliance to be retained in a human body includes a lid body (2), a connecting plug body (1), and a hinge (3). The lid body (2) is coupled to the connecting plug body (1) through the hinge (3). The connecting plug body (1), hinge (3), and lid body (2) are integrally formed of the same synthetic resin material. The lid body (2) is provided on a center area on an inner face thereof with an engaging member (4) made of a resilient material. The lid body (2) is provided on an end thereof with a strap (5).

6 Claims, 5 Drawing Sheets

CAP FOR MEDICAL APPLIANCE TO BE RETAINED IN HUMAN BODY

BACKGROUND OF THE INVENTION

(1) Field of the Invention

This invention relates to a cap which serves as an external switch valve for a medical appliance to be retained in a human body (for example, a urethra catheter and the like).

(2) Statement of the Prior Art

Heretofore, there are the following examples of medical appliances which are retained in a human body.

Various diseases involving incontinence affect women. Medical therapy including ubrechide, α-blocker and the like may be applied and an intermittent self-withdrawing method are now also widely effected. Also, a medical therapy (anticholine agent, imipramine, epohedrine hydrochloride, α actuation agent or the like), a balloon catheter retaining method, pelvis lower muscle training method, intermittent self-withdrawing method, urination method using a urine collector or various kinds of napkins, and the like are also employed in cases of incontinence. These methods have provided substantial benefits.

On the other hand, in the case of damage to cerebral blood vessels on the spinal cord, medication may be slow and people thus afflicted may have difficulty using a catheter, consequently the above methods are not often applied to these persons. In particular, women suffering paralysis having diseases worse than a middle degree and upper spinal cord (higher than seventh cervical vertebrae) damaged women are treated only by a selectable urination control method such as utilization of urinary bladder bags or napkins.

Moreover, in the case of using the urethra catheter, fine crystals are generated after the urine on the cap is dried. When the crystals are attached to contact faces of the cap, the contact faces will become rough, thereby causing leakage of urine.

SUMMARY OF THE INVENTION

An object of the present invention is to provide a cap for a medical appliance to be retained in a human body, which can be readily handled for charging and discharging urine even by, for example, women who retain urine in their bladders and find it difficult to discharge the urine and also for women who are unable to use urinary bladder bags or napkins, and which does not cause leakage of urine even if the contact surfaces become rough on account of urine crystals.

In order to achieve the above object, a cap for a medical appliance to be retained in a human body in accordance with the present invention, includes a lid body, a connecting plug body, and a hinge. The lid body is coupled to the connecting plug body through the hinge. The connecting plug body, the hinge, and the lid body are integrally formed of the same synthetic resin material. The lid body is provided on a center area on an inner surface thereof with an engaging member made of a resilient material. The lid body is provided on an end thereof with a strap. The lid body covers a top of the connecting plug body by means of an elastic recovery force of the hinge when the strap is pulled to the connecting plug body, so that the engaging member engages with a peripheral edge of an outlet port in the connecting plug body in an airtight manner.

An annular magnet may be secured to the upper face of the connecting plug body. Another annular magnet may be secured to the inner surface of the lid body around the engaging member. Preferably, the annular magnets are set to be 5 to 15 mm in diameter, 0.5 to 5.0 mm in thickness, and 100 to 2000 gauss in magnetic flux density. Magnetic poles on contact faces of the annular magnets are directed in opposition to each other.

In the cap for a medical appliance to be retained in a human body in accordance with the present invention, when a disabled patient hooks the strap to his or her palm or finger to the connecting plug body, the lid body covers a top of the connecting plug body by means of an elastic recovery force of the hinge, so that the engaging member engages with a peripheral edge of an outlet port in the connecting plug body in an airtight manner. At this time, even if the lid body moves eccentrically, the engaging member on the inner face of the lid body is guided by the outlet port in the connecting plug body to bring the lid body into a regular position. Accordingly, the lid body firmly engages with the connecting plug body and leakage of urine can be prevented since the engaging member seals the outlet port in an airtight or liquidtight manner even if any clearance between the contact faces of the bodies is caused.

In the case of opening the lid body, the lid body will be opened by pulling the strap in the reverse direction against an elastic resistant force of the hinge. When the lid body is turned over a critical angle, the lid body is maintained in a completely open position by means of a buckling action of the hinge.

In the case where the magnets are attached to the connecting plug body and lid body, respectively, the magnets will be attached to each other in their regular positions by their magnetic attractive actions when they approach each other.

Since both magnets are set to be 100 to 2000 gauss in magnetic flux density, a mutual attraction force of the magnets becomes stronger and the cap is not disconnected from the connecting plug body in use. However, in the case that the patient wants to disconnect the cap, the patient can easily detach the cap from the plug body only by pulling the strap by using his or her palm or finger.

Since it is possible to detachably connect the connecting plug body to a port of the medical appliance to be retained in the human body, the cap can be applied to the same or different kind of appliance.

Since both magnets are set to be 5 to 15 mm in diameter and 0.5 to 5.0 mm in thickness, the cap becomes relatively small and does not impart any discomfort to the patient.

DETAILED DESCRIPTION OF THE PREFERRED EMBODIMENTS

Figure 1:
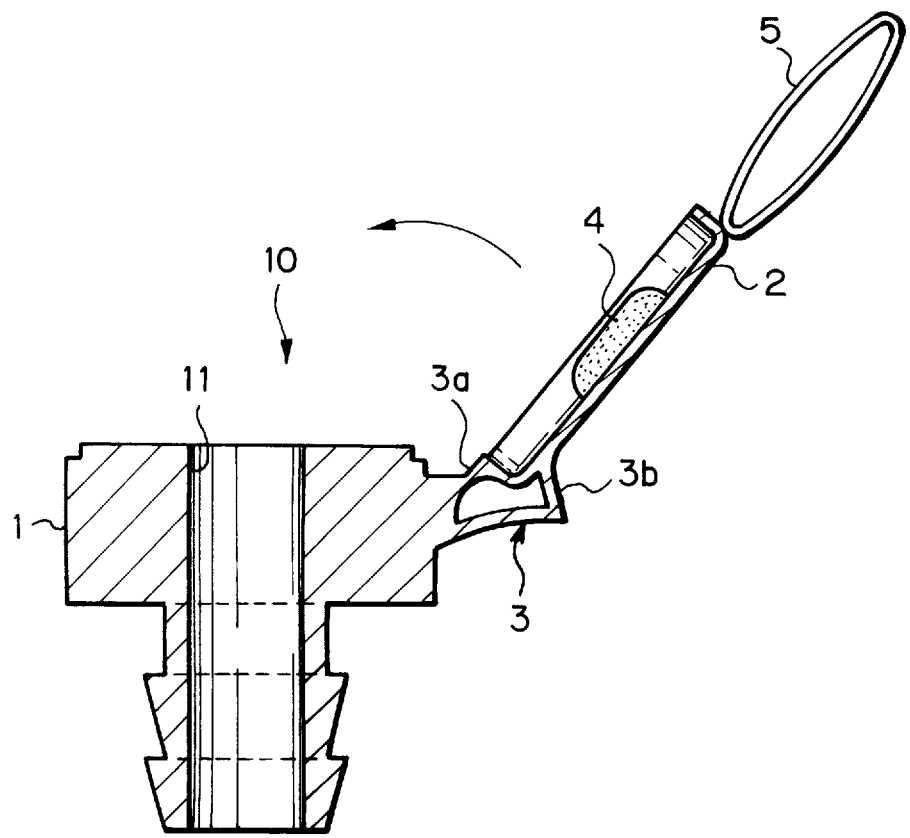
FIG. 1 is a longitudinal sectional view of an embodiment of a cap for a medical appliance to be retained in a human body in accordance with the present invention.

Referring now to FIGS. 1 through 9, embodiments of a cap 10 for a medical appliance to be retained in a human body in accordance with the present invention will be explained below.

<First Embodiment>

FIGS. 1 through 4 show a first embodiment of a cap 10 of the present invention.

As shown in FIGS. 1 to 4, the cap 10 includes a connecting plug body 1, a lid body 2, and a hinge 3. The lid body 2 is coupled to the connecting plug body 1 through the hinge 3. In the cap 10, the connecting plug body 1, hinge 3, and lid body 2 are integrally formed of the same synthetic resin material. The lid body 2 is provided on a center area on an inner surface thereof with an engaging member 4 made of a resilient material (for example, silicon rubber, polyethylene, or the like). The lid body 2 is provided on an end thereof with a strap 5.

Figure 2:
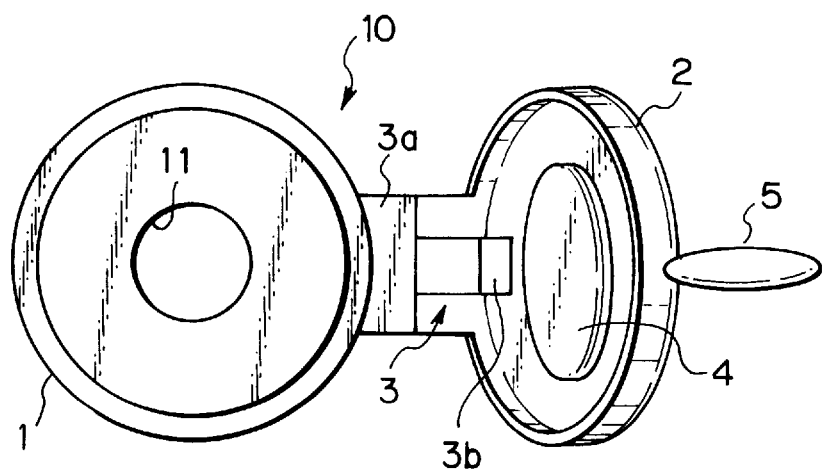
FIG. 2 is a plan view of FIG. 1.
Figure 3:
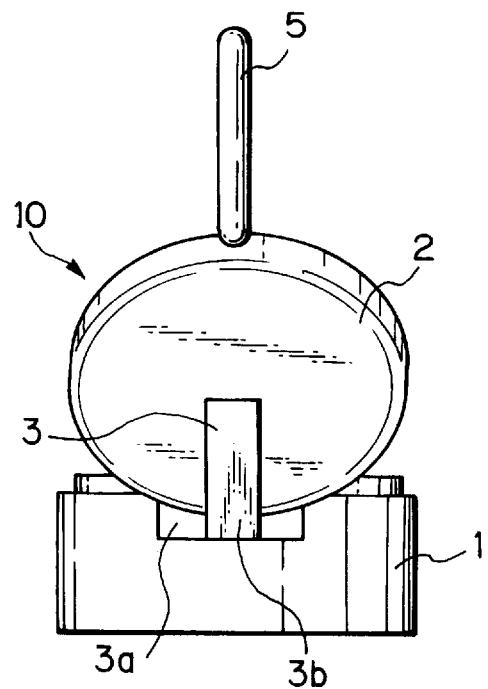
FIG. 3 is a rear elevational view of FIG. 1.

The hinge 3, as shown in FIGS. 1 to 3, includes a joint portion 3a which serves to join the lid body 2 to the connecting plug body 1, an elastically deformable portion 3b. The elastically deformable portion 3b actuates the lid body 2 to be closed by the elastic recovery force within a critical turning angle, but the portion 3b actuates the lid body 2 to be returned to the completely open position by means of the buckling action of the portion 3b when the lid body 2 rotates over the critical turning angle (see FIG. 1).

Figure 4:
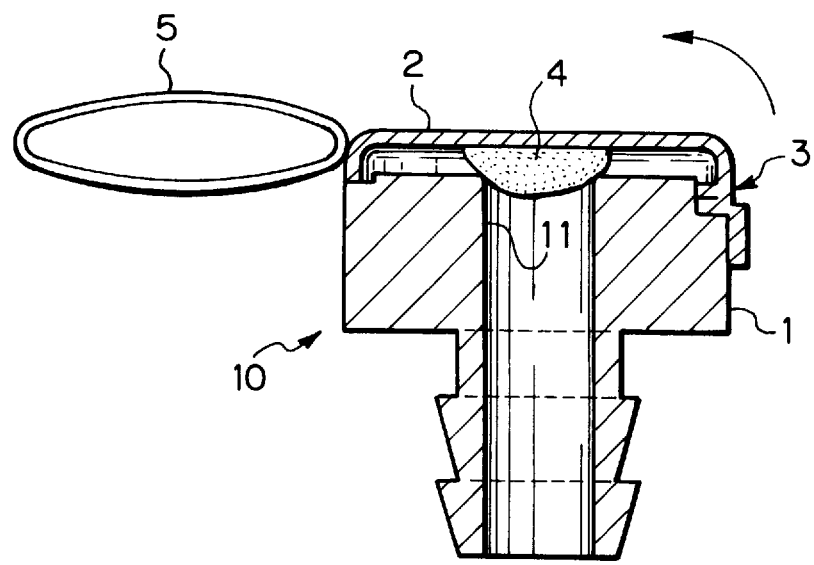
FIG. 4 is a longitudinal sectional view of the cap shown in FIG. 1, illustrating a closed position of a lid body of the cap.

As shown in FIG. 4, the engaging member 4 engages with a peripheral edge of an outlet port 11 in the connecting plug body 1 with the member 4 being resiliently deformed when the lid body 2 covers a top of the connecting plug body 1, thereby maintaining the outlet port 11 in an airtight or liquidtight condition.

Even if a person has limited use of hands or fingers, the lid body can be easily opened and closed by hooking and pulling the strap 5 by a person's palm or finger.

The cap 10 may be used, for example, as shown in FIGS. 7A and 7B. FIG. 7A shows an example in which the cap 10 is attached to an external drain port of an usual urethra catheter 20. FIG. 7B shows another example in which the cap 10 is attached to an external drain port of an usual MALECOT catheter 30.

Although the connecting plug body shown in FIGS. 1 to 4 is coupled to an inside of a port of a mating appliance, the connecting plug body may be coupled to the outside of the port.

<Second Embodiment>

Next, a second embodiment of a cap for a medical appliance to be retained in a human body in accordance with the present invention will be explained below by referring to FIGS. 5 to 6 and FIGS. 8 to 9.

In the second embodiment, an annular magnet 6 is secured to the upper face of the connecting plug body 1 and another annular magnet 7 is secured to the inner face of the lid body 2 around the engaging member 4. The magnets 6 and 7 are set to be 5 to 15 mm in diameter, 0.5 to 5.0 mm in thickness, and 100 to 2000 gauss in magnetic flux density. Magnetic poles on contact faces of the magnets 6 and 7 are directed in opposition to each other. In the illustrated embodiment, the upper and lower faces of the annular magnet 6 are set to be an S-pole and an N-pole while the upper and lower faces of the magnet 7 are set to be an N-pole and an S-pole.

Figure 5:
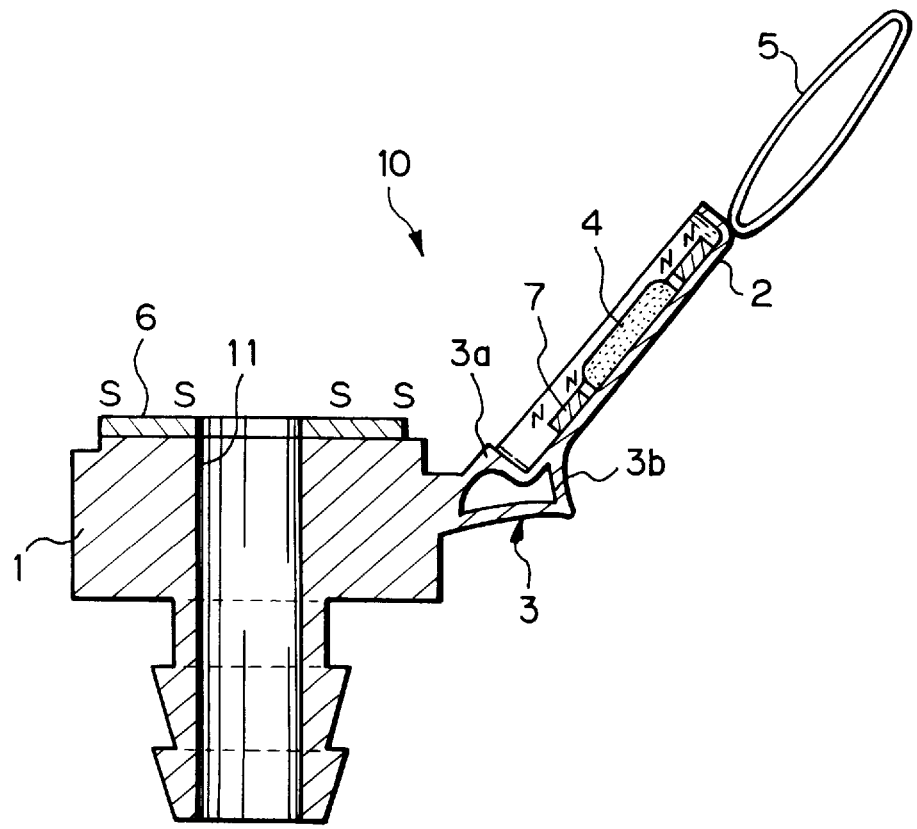
FIG. 5 is a longitudinal sectional view of another embodiment of the cap for the medical appliance to be retained in a human body in accordance with the present invention.
Figure 6:
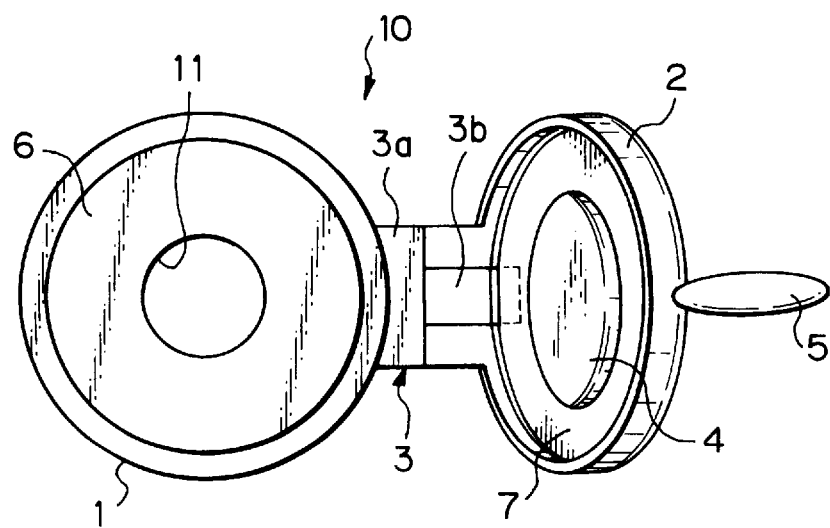
FIG. 6 is a plan view of FIG. 5.
Figure 7:
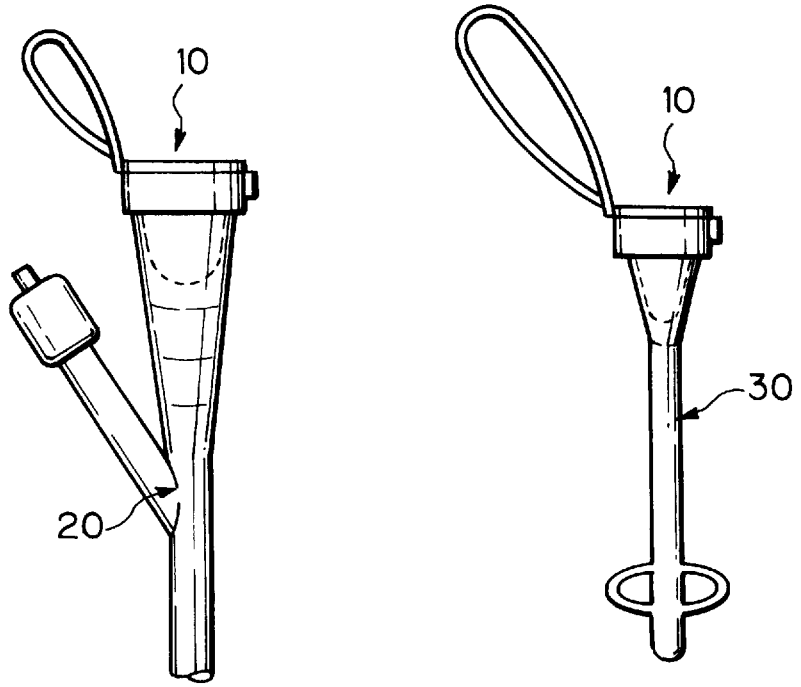
FIGS. 7A and 7B are side elevational views of the cap of the present invention, illustrating examples of using the cap.

As shown in FIGS. 5 and 6, when the cap 10 is in an open position the annular magnet 6 releases the outlet port 11 in the connecting plug body 1 while the magnet 7 is spaced away from the body 1.

Figure 8:
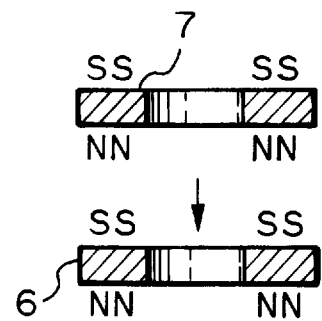
FIG. 8 is an explanatory view illustrating an operation of the cap shown in FIG. 5.

As shown in FIG. 9A, when the cap is in a closed position, both magnets 6 and 7 make contact with each other and attract each other by their magnetic forces. As shown in FIG. 8, both magnets 6, 7 are aligned with the same center axis by their attraction forces immediately before the magnets 6, 7 make contact with each other. Even if the magnets are a little shifted from each other, the engaging member 4 can automatically correct the misalignment in a manner described above.

In the case that one of the magnets 6 and 7 is made of an iron material, they immediately make contact with each other when they approach each other and thus they cannot adjust the misalignment of their center axes automatically.

Figure 9:
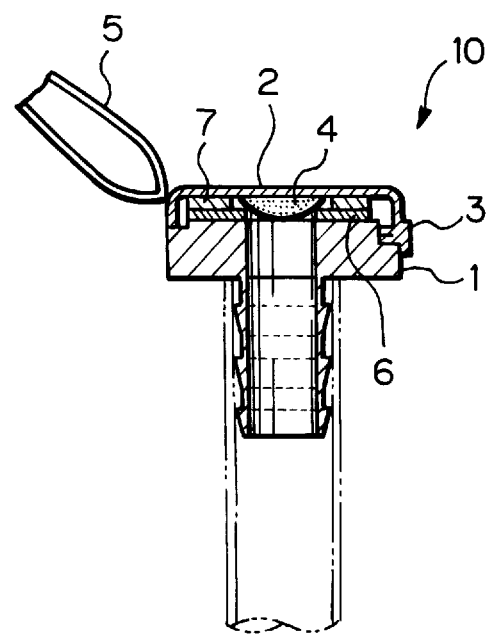
FIG. 9 is a longitudinal sectional view of the cap shown in FIG. 5, illustrating a closed position of a lid body of the cap.

When the cap 10 is in the closed position as shown in FIG. 9, the engaging member 4 closes the outlet port 11 in the connecting plug body 1.

When the magnets 6 and 7 are attached to each other, the engaging member 4 inside the annular magnet 7 makes contact with the inner peripheral edge of the annular magnet 6 and the inner peripheral edge of the outlet port 11 in the connecting plug body 1, thereby enhancing the air and liquid sealing in the cap 10 (FIG. 9). In addition, the engaging member 4 serves to guide the magnet 7 upon interconnection of the magnets 6 and 7.

Applications shown in FIGS. 7A and 7B can be also applied to the second embodiment.

A medical appliance, in particular, a MALECOT catheter to which the magnetic cap of the present invention can be applied is limited to the following diseases of patients:

1. It is preferable that the patient has a desire to urinate. It is not suitable for use in cases of dementia.
2. The patient can bring one's finger to the vulva.
3. A capacity of the urinary bladder must be more than 150 ml.
4. The patient can balance upon opening the legs and sitting on the legs.
5. It is not suitable for the patient who has an external port of the urethra in one's inner part or has pronounced vagina atrophy.
6. It is not suitable for a patient who feels that a balloon catheter retained in the body is an obstacle.
7. The patient may take a bath.
8. It is applicable for a patient who has difficulty in moving ones fingers, has urination diseases or urine storage diseases.
9. The patient can urinate at a toilet under a condition similar to natural urination.

The magnetic cap of this invention can be utilized to a medical appliance to be retained in a human body over a wide scope, is simple in operation, and is superior in a closing function. Even if the contact surfaces of the cap become rough on account of the crystals of urine, any leakage of urine will not occur. Further, the cap has a simple construction and can be made at a low production cost.

What is claimed is:

1. A cap for a medical appliance to be retained in a human body, wherein a lid body is coupled to a connecting plug body through a hinge, characterized in that:

said connecting plug body, said hinge, and said lid body are integrally formed of a same synthetic resin material;

said lid body has an inner surface with a center area and is provided with an engaging member being made of a resilient material, said engaging member being located on said center area of said inner surface;

said lid body is provided with a strap located on an end of said lid body;

said connecting plug body has an upper face with an outlet port, said outlet port having a peripheral edge; and said lid body covers said upper face by means of an elastic recovery force of said hinge when said strap is pulled to said connecting plug body, so that said engaging member engages with said peripheral edge of said outlet port in said connecting plug body in an airtight manner, wherein an annular magnet is secured to the upper face of said connecting plug body, another annular magnet is secured to the inner surface of said lid body around said engaging member, said annular magnets being 5 to 15 mm in diameter, 0.5 to 5.0 mm in thickness, and 100 to 2000 gauss in magnetic flux density, and magnetic poles on contact surfaces of said annular magnets are directed in opposition to each other.

2. A cap according to claim 1, wherein said hinge includes a joint portion and an elastically deformable portion which actuates said lid body to move to a closed position by the elastic recovery force when said lid body is rotated within a critical turning angle, and actuates said lid body to move to a completely open position by means of a buckling action of said elastically deformable portion when said lid body rotates over the critical turning angle.

3. A cap according to claim 1, wherein the medical appliance is a urethra catheter.

4. A cap according to claim 1, wherein the medical appliance is a MALECOT catheter.

5. A cap according to claim 1, wherein said resilient material is selected from the group consisting of silicon rubber and polyethylene.

6. A cap for a medical appliance to be retained in a human body, wherein a lid body is coupled to a connecting plug body through a hinge, being characterized in that:

said connecting plug body, said hinge, and said lid body are integrally formed of a synthetic resin material;

said lid body has an inner surface with a center area and is provided with an engaging member made of a resilient material, said engaging member being located on said center area of said inner surface;

said lid body is provided with a strap located on an end of said lid body;

said connecting plug body has an upper face with an outlet port, said outlet port having a peripheral edge; and said lid body covers said upper face by means of an elastic recovery force of said hinge when said strap is pulled to said connecting plug body, so that said engaging member engages with said peripheral edge of said outlet port in said connecting plug body in an airtight manner, wherein an annular magnet is secured to the upper face of said connecting plug body, another annular magnet is secured to the inner surface of said lid body around said engaging member, and magnetic poles on contact surfaces of said annular magnets are directed in opposition to each other.

\* \* \* \* \*